United States Patent
Park et al.

(10) Patent No.: US 12,093,873 B2
(45) Date of Patent: Sep. 17, 2024

(54) USER PERFORMANCE ANALYSIS AND CORRECTION FOR S/W

(71) Applicant: INTERNATIONAL BUSINESS MACHINES CORPORATION, Armonk, NY (US)

(72) Inventors: Sun Young Park, San Diego, CA (US); Srivenkata Laksh Gantikota, San Diego, CA (US); Dustin Michael Sargent, San Diego, CA (US); Marwan Sati, Mississauga (CA)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 17/156,123

(22) Filed: Jan. 22, 2021

(65) Prior Publication Data
US 2022/0237540 A1 Jul. 28, 2022

(51) Int. Cl.
*G06Q 10/0639* (2023.01)
*G06N 20/00* (2019.01)
(Continued)

(52) U.S. Cl.
CPC ......... *G06Q 10/0639* (2013.01); *G06N 20/00* (2019.01); *G06Q 10/063112* (2013.01); *G16H 30/20* (2018.01)

(58) Field of Classification Search
CPC ....... G06Q 10/0639; G06Q 10/063112; G16H 30/00; G06N 20/00
See application file for complete search history.

(56) References Cited

U.S. PATENT DOCUMENTS

| 6,401,111 B1 * | 6/2002 | Dan ........................ H04L 43/00 709/224 |
| 8,645,387 B2 | 2/2014 | Hiltz-Laforge et al. |

(Continued)

FOREIGN PATENT DOCUMENTS

| CA | 2776229 A1 * | 11/2012 | ............. G06Q 50/16 |
| WO | WO-2009057156 A2 * | 5/2009 | ......... H04L 63/0492 |

OTHER PUBLICATIONS

Vincenzo, D. F., Dignös, A., Raimato, G., Maccioni, L., Borgianni, Y., & Gamper, J. (2019). Visual time period analysis: A multimedia analytics application for summarizing and analyzing eye-tracking experiments. Multimedia Tools and Applications, 78(23), 32779-32804. (Year: 2019).*

(Continued)

*Primary Examiner* — Patricia H Munson
*Assistant Examiner* — Nicholas D Bolen
(74) *Attorney, Agent, or Firm* — Yee & Associates, P.C.

(57) ABSTRACT

Methods and systems for optimizing user interaction with a software application. One system includes an electronic processor configured to receive a collection of interaction data including a plurality of interaction sequences and data associated with each of the plurality of interaction sequences, determine a performance metric for each of the plurality of interaction sequences, and train, with the collection of interaction data and the performance metric determined for each of the plurality of interaction sequences, an artificial intelligence ("AI") model using supervised learning. The electronic processor is also configured to receive a current interaction sequence of a user for the software application and generate, via the AI model as applied to the interaction pattern of the user, a recommendation, for display within a user interface, for a modified user interaction pattern of the user for the software application.

19 Claims, 8 Drawing Sheets

(51) Int. Cl.
*G06Q 10/0631* (2023.01)
*G16H 30/20* (2018.01)

(56) References Cited

U.S. PATENT DOCUMENTS

| | | | |
|---|---|---|---|
| 9,218,430 B2 | 12/2015 | Forte | |
| 9,710,787 B2 | 7/2017 | Mabogunje et al. | |
| 10,303,511 B2 | 5/2019 | Moulden et al. | |
| 10,664,041 B2 | 5/2020 | Flores et al. | |
| 10,732,803 B2 | 8/2020 | Duffield et al. | |
| 2002/0105532 A1* | 8/2002 | Oblinger | G06Q 30/06 707/E17.143 |
| 2005/0132381 A1* | 6/2005 | Fiammante | G06F 8/24 719/310 |
| 2007/0162505 A1* | 7/2007 | Cecchi | G06F 16/907 |
| 2014/0195297 A1* | 7/2014 | Abuelsaad | G06Q 10/0635 705/7.28 |
| 2015/0271281 A1 | 9/2015 | Sundqvist et al. | |
| 2015/0356061 A1 | 12/2015 | Rampson et al. | |
| 2016/0274902 A1* | 9/2016 | Mehrotra | G06Q 10/101 |
| 2017/0075506 A1* | 3/2017 | O'Doherty | G06F 9/44 |
| 2017/0083821 A1 | 3/2017 | Foerster et al. | |
| 2018/0300621 A1* | 10/2018 | Shah | G06N 3/044 |
| 2019/0042627 A1 | 2/2019 | Osotio et al. | |
| 2019/0050588 A1* | 2/2019 | Brew | G06N 20/00 |
| 2019/0129940 A1* | 5/2019 | Hewitt | G06N 5/02 |
| 2019/0138973 A1* | 5/2019 | Akella | G06N 3/04 |
| 2019/0147366 A1* | 5/2019 | Sankaran | G06N 3/04 706/12 |
| 2019/0171726 A1* | 6/2019 | Ahmed | G06F 16/9535 |
| 2019/0286426 A1 | 9/2019 | Anicic | |
| 2019/0286436 A1 | 9/2019 | Anicic et al. | |
| 2019/0392077 A1 | 12/2019 | Kikuchi | |
| 2020/0134143 A1 | 4/2020 | Deole et al. | |
| 2020/0134488 A1 | 4/2020 | Kim et al. | |

OTHER PUBLICATIONS

Guimbretiere et al., "ExperiScope: An Analysis Tool for Interaction Data", Proceedings of the 2007 Conference on Human Factors in Computing Systems, CHI 2007, San Jose, California, USA, Apr. 28-May 3, 2007, pp. 1333-1342.

Wörndl et al., "Selecting Gestural User Interaction Patterns for Recommneder Applications on Smartphones", 7th ACM Conference on Recommender Systems, Oct. 12-16, 2013, pp. 17-20.

Mehrotra et al., "Understanding the Role of Places and Activities on Mobile Phone Interaction and Usage Patterns", Proceeding of the ACM on Interact. Mob. Wearable Ubiquitous Technol., Sep. 2017, vol. 1, Issue 3, Article 84, pp. 1-22.

Vega-Barbas et al., "Interaction Patterns for Smart Spaces: A Confident Interaction Design Solution for Pervasive Sensitive IoT Services", IEEE Access, Nov. 27, 2017, vol. 6, pp. 1126-1136.

Andrews et al., "Modeling Collaborative Interaction Patterns in a Simulation-Based Task", Journal of Educational Measurement, Mar. 6, 2017, vol. 54, No. 1, pp. 54-59.

Dikici et al., "Integrating AI into radiology workflow: levels of research, production, and feedback maturity", Feb. 11, 2020, Journal of Medical Imaging, vol. 7, Issue 1, 016502 (Feb. 2020), doi: 10.1117/1.JMI.7.1.016502, 13 pages.

Long, Marlee, "PACS RIS and AI: a fully integrated radiology workflow", aidoc, downloaded from the Internet on Jan. 23, 2023, 7 pages, <https://www.aidoc.com/blog/pacs-ris-ai-workflow/>.

* cited by examiner

USER PERFORMANCE ANALYSIS AND CORRECTION FOR S/W

FIELD

Embodiments described herein generally relate to modeling user interactions with software applications, such as via artificial intelligence techniques, wherein the resulting model may be used to compare one user's interactions with interactions of other users (or recommended interaction sequences) and generate and output optimized software interactions for the user. In other words, embodiments described herein provide personalized software usage optimization using user interaction information. For example, embodiments described herein may generate and provide a suggestion to a user, wherein the suggestion includes a new workflow (i.e., a new interaction pattern) for improving the user's efficiency with respect to the software application.

SUMMARY

Radiologists play an important role in the medical imaging field. A radiologist's productivity, however, may be influenced by the physician's reading style, expertise, exam type, software tools, workflow process, or the like. While efficiency of radiologists is important, so is diagnostic performance, such as accuracy. Lack of appropriate training, habits and routines, and the like may limit efficiency and performance in ways that are not apparent to the radiologist. Similar issues may arise in other fields, including, for example, a gaming application where gaming performance may be negatively impacted by factors that are under the user's control but are not related to human error. For example, a keyboard shortcut may exist for a particular maneuver or function within the gaming application, that the user may be unaware of and, thus, may be performing the same maneuver using a less efficient sequence of actions. In general, regardless of the field or industry, it may be difficult for users of a software application to self-evaluate and determine the appropriate steps to fix issues or improve their interaction and use with the software application. These issues may arise from suboptimal preferences, bias, or stubbornness.

Accordingly, embodiments described herein track user interaction patterns for a particular software application and associated user performance metrics and use the tracked patterns to train a model (for example, using artificial intelligence techniques). The model, as trained, may then be applied to a particular user's interaction pattern to effectively compare the user's interaction pattern to interaction patterns for "experts" (for example, users with particular performance metrics, such as highest diagnostic accuracy) to identify inefficient or other sub-optimal interaction patterns of the user and provide recommendations for addressing the same.

For example, embodiments described herein use deep learning to automatically determine (via a trained model) interaction patterns associated with expert users. Other users (for example, new users) may then be assessed using the generated model. Various performance metrics may be used to identify ground truth at a user level. For example, high diagnostic accuracy may be used to identify an "expert" radiologist using a Picture and Archiving Communication System ("PACS") viewer. This ground truth may be used to train a model, wherein interactions performed by this "expert" are indicative of a high skill level. After being trained, the model may be used to identify inefficient interaction patterns and correct such user behavior.

Other aspects will become apparent by consideration of the detailed description and accompanying drawings.

DETAILED DESCRIPTION

Before any embodiments are explained in detail, it is to be understood that the embodiments are not limited in their application to the details of construction and the arrangement of components set forth in the following description or illustrated in the following drawings. Other embodiments are capable of being practiced or of being carried out in various ways.

Also, it is to be understood that the phraseology and terminology used herein is for the purpose of description and should not be regarded as limiting. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and may include electrical connections or coupling, whether direct or indirect. Also, electronic communications and notifications may be performed using any known means including direct connections, wireless connections, etc.

A plurality of hardware and software based devices, as well as a plurality of different structural components may be utilized to implement the embodiments. In addition, embodiments may include hardware, software, and electronic components or modules that, for purposes of discussion, may be illustrated and described as if the majority of the components were implemented solely in hardware. However, one of ordinary skill in the art, and based on a reading of this detailed description, would recognized that, in at least one embodiment, the electronic-based aspects of the embodiments may be implemented in software (for example, stored on non-transitory computer-readable medium) executable by one or more processors. As such, it should be noted that a plurality of hardware and software based devices, as well as a plurality of different structural components, may be utilized to implement the embodiments. For example, "mobile device," "computing device," and "server" as described in the specification may include one or more electronic processors, one or more memory modules including non-transitory computer-readable medium, one or more input/output interfaces, and various connections (for example, a system bus) connecting the components.

As noted above, embodiments described herein track user interactions with a software application and apply a model to such interactions to assess whether the user interactions are optimal (for example, based on the particular user's role and task being performed). Sub-optimal interactions may be identified and corrected, such as by recommending that a user alter his or her sequence of interactions within the software application to perform a particular task.

Figure 1:
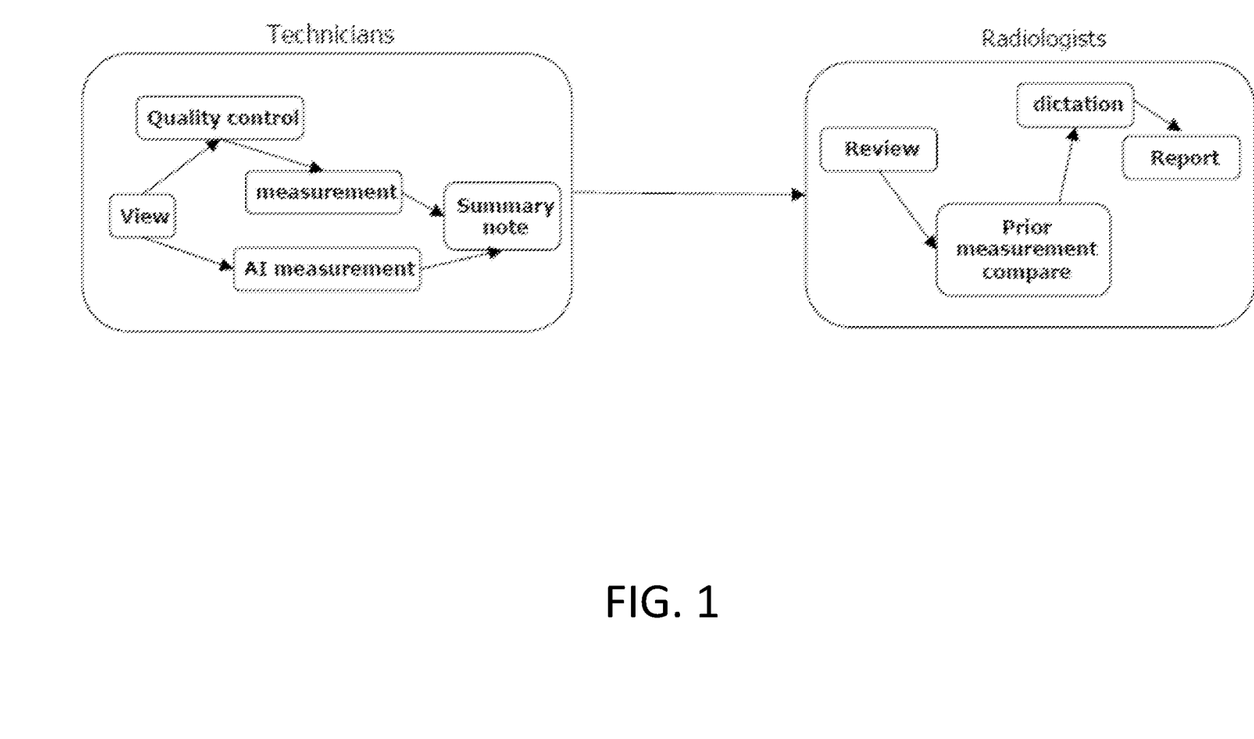
FIG. 1 illustrates example tasks performed by different user roles via a software application according to some embodiments.

It should be understood that "software application" as used in the present application may refer to a complete software application, such as a medical imaging application, or a particular feature or tool within the same. Users with various user roles may interact with the software application to perform one or more tasks. As one example, as illustrated in FIG. 1, when the software application is a medical imaging application, users having a role of "technicians" and users having a role of "radiologists" may both use the same software application to complete various tasks. In particular, as illustrated in FIG. 1, a technician may use the software application to create a "summary note," and a radiologist may use the "summary note" created by a technician to create a "report." Users with different user roles may perform the same or different tasks using the same software application, and completing a particular task may involve a different set of interactions, a different sequence of interactions, or a combination thereof depending on the role of the user completing the task. Also, as discussed below, there may be different ways to perform the same task (for the same or different user roles) and embodiments described herein may identify an optimal way (pattern or sequence of interaction) for completing a particular task by tracking and analyzing how different users perform the same task.

As noted above, embodiments described in the present application may be used with medical-related software applications, such as medical imaging software, or with other types of software applications, including, for example, gaming applications or other software applications where different user interactions result in different usage levels of the software application (for example, different efficiency, different performance, different accuracy, or the like). It should also be understood that "user interactions," "user activities," or "user actions" as these terms are used in the present application, refer to input from a user into the software application and may include, for example and without limitations, mouse clicks, text input, keyboard shortcuts, menu navigations and selections, voice-activated commands, gestures, and the like. It should also be understood that the software application may be executed locally on a device owned or operated by the user or may be executed remotely, such as on a server accessible by the user over one or more communication networks. Further details regarding possible system configurations are discussed below with respect to FIG. 8.

Figure 2:
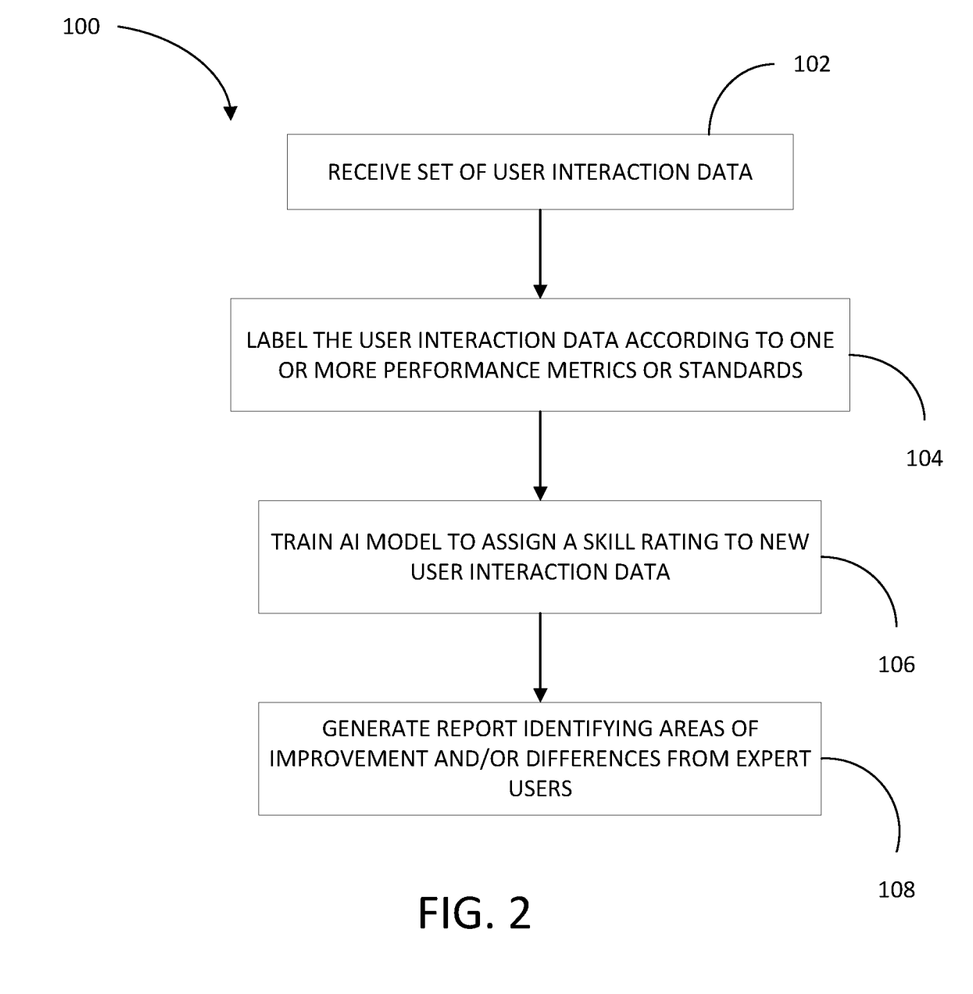
FIG. 2 illustrates a method of optimizing a user's interaction pattern with a software application using artificial intelligence according to some embodiments.

FIG. 2 illustrates a method 100 of optimizing a user's interaction pattern with a software application using artificial intelligence. The method 100 is described herein in terms of a medical imaging software application, such as a PACS viewer and report generation software application. However, as noted above, the method 100 may be used with other types of software applications.

The method 100 includes receiving a set of user interaction data with the software application (at 102). In some embodiments, the user interaction data includes interactions with the software application for various imaging modalities performed by different users and, in some embodiments, related to performing one or more tasks. In some embodiments, to ensure that the set of user interaction data includes examples for each task, each user role, or both, the start and end points of user interactions with the software application for different types of exams and different types of user roles may be identified (for example, from logs, software requirement documentation, and the like). As noted above, different user roles may perform the same or different tasks and may perform the same tasks in different ways. Similarly, tasks performed for an image study may be performed different based on the type of image study, such as, for example, the exam type (for example, body part, modality, diagnostic or screening, or the like).

The exams used within the software application may also be classified, such as by body part, imaging modality, diagnostic status (for example, diagnostic or screening purpose), prior patient history, or the like. Again, as described below in more detail, different user interaction patterns may be associated with different types of exams. As one example, an efficient and accurate user interaction pattern by an expert radiologist for reviewing one type of exam may vary from an efficient and accurate interaction pattern by an expert radiologist for reviewing a different type of exam (even the same expert). Similar differences may exist depending on whether the exam was generated for diagnostic purposes or screening purposes, the image modality used to generate the exam, the type of patient associated with the exam, or the like. Thus, classifying an exam associated with particular user interactions allows the model to more accurately identify inefficient user interaction patterns.

After identifying these sequences (for example, the start and end points of interaction), a large set of examples of these sequences may be identified for use as training data from the received set of user interaction data. This set of examples may be pulled from various logs or other tracked information including user interaction data, which tracks user activities (for example, exam selection, menu selections, tool selections, and the like as well as timing information, such as, for example, log-in and log-out timestamps). In some embodiments, preprocessing or filtering may be performed on the set of examples, such as to eliminate "noise" (for example, outlier sequences, incomplete sequences, sequences expanding more than a predetermined amount of time, or the like).

In some embodiments, each example may be classified or labeled according to an exam type, the user role, the task being performed, and the like. In some embodiments, imaging exam information is retrieved for an image study associated with a particular example (for example, using an image study identifier associated with tracked user interactions) and used to classify an example as being associated with a particular exam type. Similarly, user information may be retrieved for a user associated with a particular example (for example, using a user identifier associated with tracked user interactions) and used to classify an example as being associated with a particular user role.

As illustrated in FIG. 2, each example included in this set is also labeled according to an expertise level, one or more performance dimensions (for example, speed, accuracy, and the like), or a combination thereof (at 104). This label may be based on a level of expertise (for example, years of experience, education level, position, and the like, which may be determined based on the specific user associated with the example and retrieved user information), a performance metric, such as accuracy or speed, or a combination thereof. Speed-based performance metrics may be determined from the example interaction pattern itself. Accuracy performance metrics may be determined by accessing diagnostic reports, test results, and the like for the exam associated with the interaction.

Figure 3:
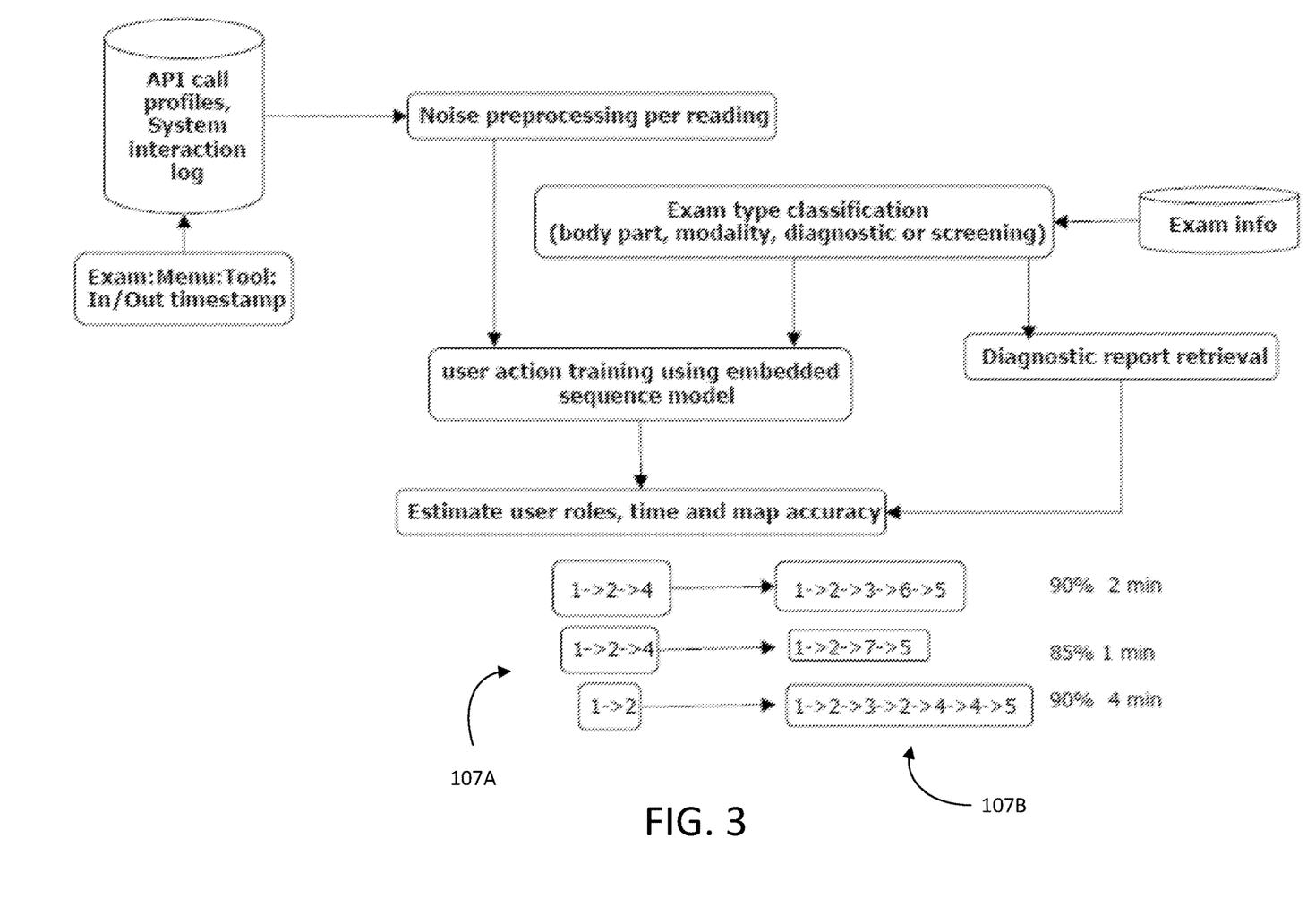
FIGS. 3-4 illustrates methods of applying the method of FIG. 2 to user interactions with the software application according to some embodiments.

The classified and labeled examples may then be used to train an artificial intelligence ("AI") model to assign skill ratings to new user interaction data (for example, with "expert" users as the gold standard) (at 106). The AI model may be a time-series deep learning model, such as, for example, a recurrent neutral network ("RNN") model, a long short-term memory ("LSTM") model, a time-based convolution network ("TCN") model, or the like. The model is trained to learn an optimal sequence of interactions performed by an "expert" user for each role, each task, and each exam type and, furthermore, learn a time required for each task and an accuracy of tasks. For example, as illustrated in FIG. 3, the model is trained to map particular sequences (for example, action 1, 2, and 4 followed by actions 1, 2, 3, 6, and 5) to a particular time and a particular accuracy (for example, 2 minutes and 90% accuracy). As illustrated in FIG. 3, in some embodiments, a sequence for a particular task may include subsequences by different user roles, such as a sequence performed by a technician (represented in FIG. 3 by reference numeral 107A) and then a sequence performed by a radiologist (represented in FIG. 3 by reference numeral 107B). Training the model using this type of subsequences allows the model to learn an optimal combination of sequences (for example, by different user roles).

Accordingly, once trained, the model may receive (as input) a sequence of actions for a particular task, a particular user role, and a particular exam and output one or more performance ratings for the user, optimization recommendations, or a combination thereof. The performance ratings may include an overall rating, a categorized performance rating, or a combination thereof. For example, the performance ratings may rank or score the user within a set of radiologists, a particular user role, or a particular exam type. Alternatively or in addition, the performance ratings may rank or score the user in terms of speed, accuracy, efficiency (for example, number of interactions), or the like. The ratings may be generated using reports, test results, or other performance measurements from the user's interaction data. In addition to the performance ratings, optimizations may be provided, such as identifications of areas of improvement for one or more users as well as differences between a particular user and an "expert" user.

Figure 4:
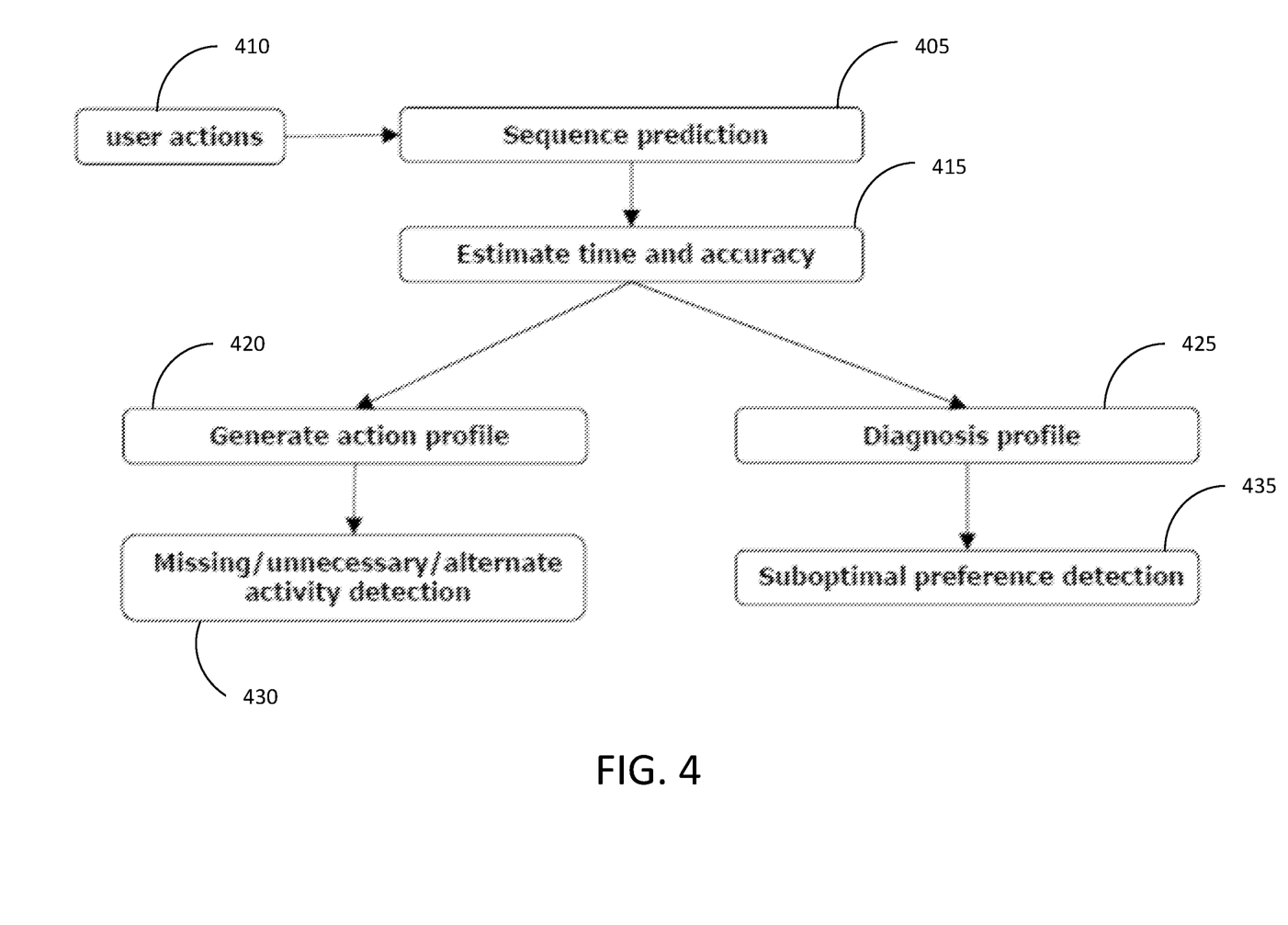

The ratings generated via the model may be included in a report that may identify one or more areas of improvement for a particular user, differences between the user's interaction and "expert" users, or a combination thereof (at 108 of FIG. 2). For example, as illustrated in FIG. 4, the model, as trained, may be used to determine or predict a sequence (i.e., a task) being performed by a particular user (at 405) based on tracked user actions (at 410) and also estimate the time and accuracy of the predicted sequence (at 415). These estimates may be used to generate one or more profiles, such as an action profile (at 420) and a diagnosis profile (at 425). The action profile may define missing, unnecessary, or alternative activity detected for the user (at 430). The diagnosis profile may define any suboptimal preferences detected, which may affect the user's accuracy or other performance metric (at 435).

The analysis performed by the model, as trained, may be performed as part of a user evaluation or training exercise (for example, on a regular or on-demand basis) as well as to provide continuous (for example, real-time) monitoring. In addition, feedback associated with user interaction patterns analyzed by the trained model may be used to not only provide updated feedback to users but also update the model (for example, through updated training with the newly-acquired feedback). Using the feedback allows a particular user's performance to be re-assessed based on known outcomes (for example, false negatives or positives, missed incidental findings, and the like).

The collection and classifying/labeling of example user interactions (used to train the model) may include one or more manual activities, which may be labor intensive and may limit the number and quality of example interactions included in the training data. For example, in some embodiments, it may be difficult for an example interaction sequence for a particular task to be identified since, as recognized above, different users may follow different workflows to perform the same task. Accordingly, in some embodiments, AI techniques may also be used to learn how to identify examples of interaction sequences for a particular task.

Figure 5:
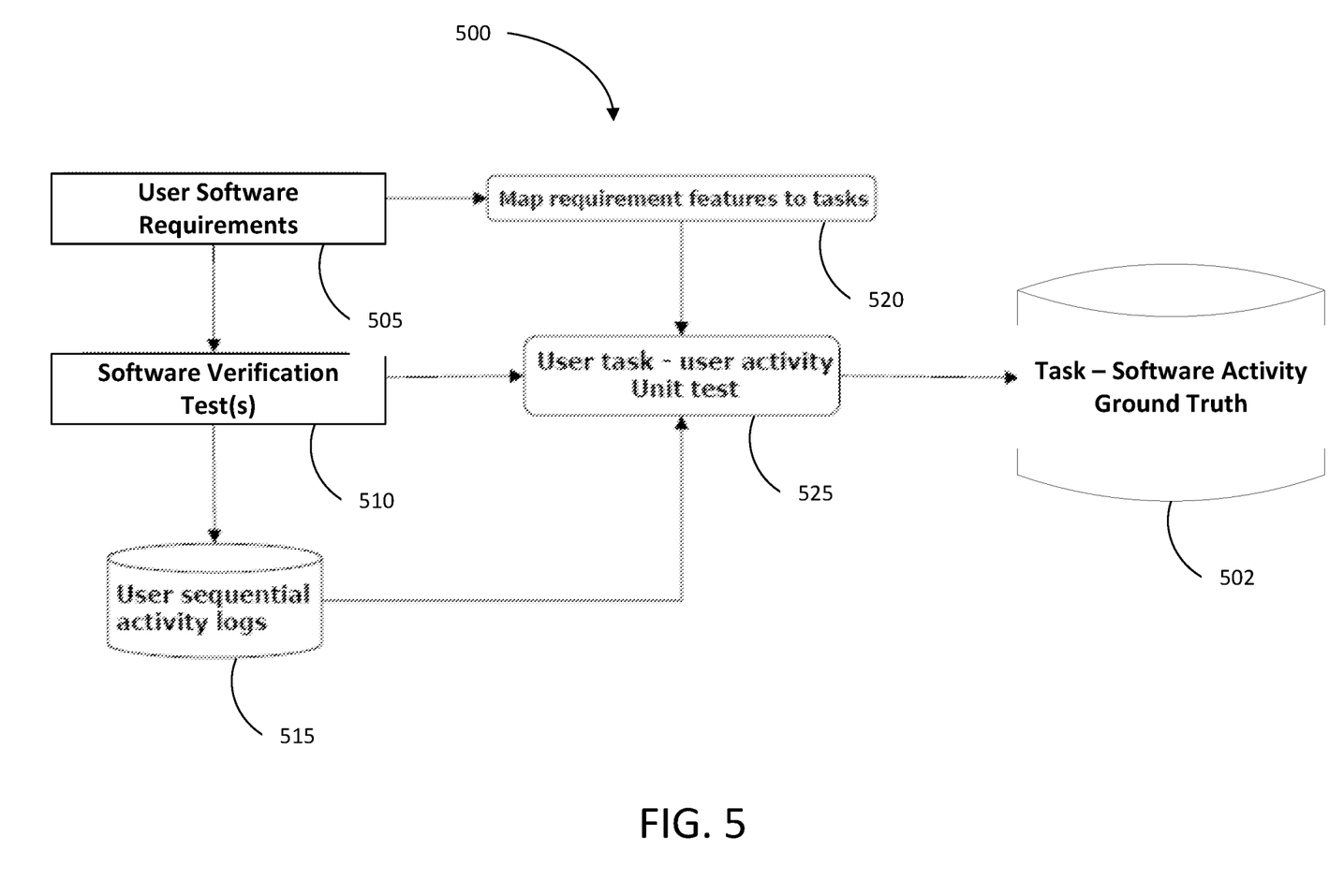
FIG. 5 illustrates a method of establishing a ground truth for a task performed via a software application according to some embodiments.

For example, FIG. 5 illustrates a method 500 of establishing a ground truth (represented in FIG. 5 by reference numeral 502) for one or more tasks performed via a software application according to some embodiments. As illustrated in FIG. 5, the ground truth 502 may be established based on user software requirements (represented in FIG. 5 by reference numeral 505). The user software requirements 505 may be defined or generated by the software developer and may define each task that may be performed within the software application.

Based on the tasks defined via the user software requirements 505, examples of each task (from a start point to an end point) may be automatically identified from the software verification tests (represented in FIG. 5 by reference numeral 510), the user sequential activity logs (represented in FIG. 5 by reference numeral 515), or a combination thereof. The software verifications tests 510 may include simulated user interactions generated as part of testing the software application, a particular feature, or a combination thereof. In comparison, the user sequential activity logs 515 may include user interactions generated as part of normal use or execution of the software application. Accordingly, the user software requirements 505 may be used to map requirement features to individual tasks for each type of user role associated with the software application (at 520), and the software verification tests 510, the user sequential activity logs 515, or combinations thereof may be used to identify example interaction sequences for each identified task (at 525). In some embodiments, additional data may be collected or generated and included as part of the identified sequence examples for each task (and each user role) included in the ground truth 502. For example, in some embodiments, statistics may be calculated for each type of action performed by each role for each task, such as, for example, a number of images scrolled, a hanging protocol used, and the like. This information (or a portion thereof) may be stored as part of the user sequential activity logs 515 or separately.

Figure 6:
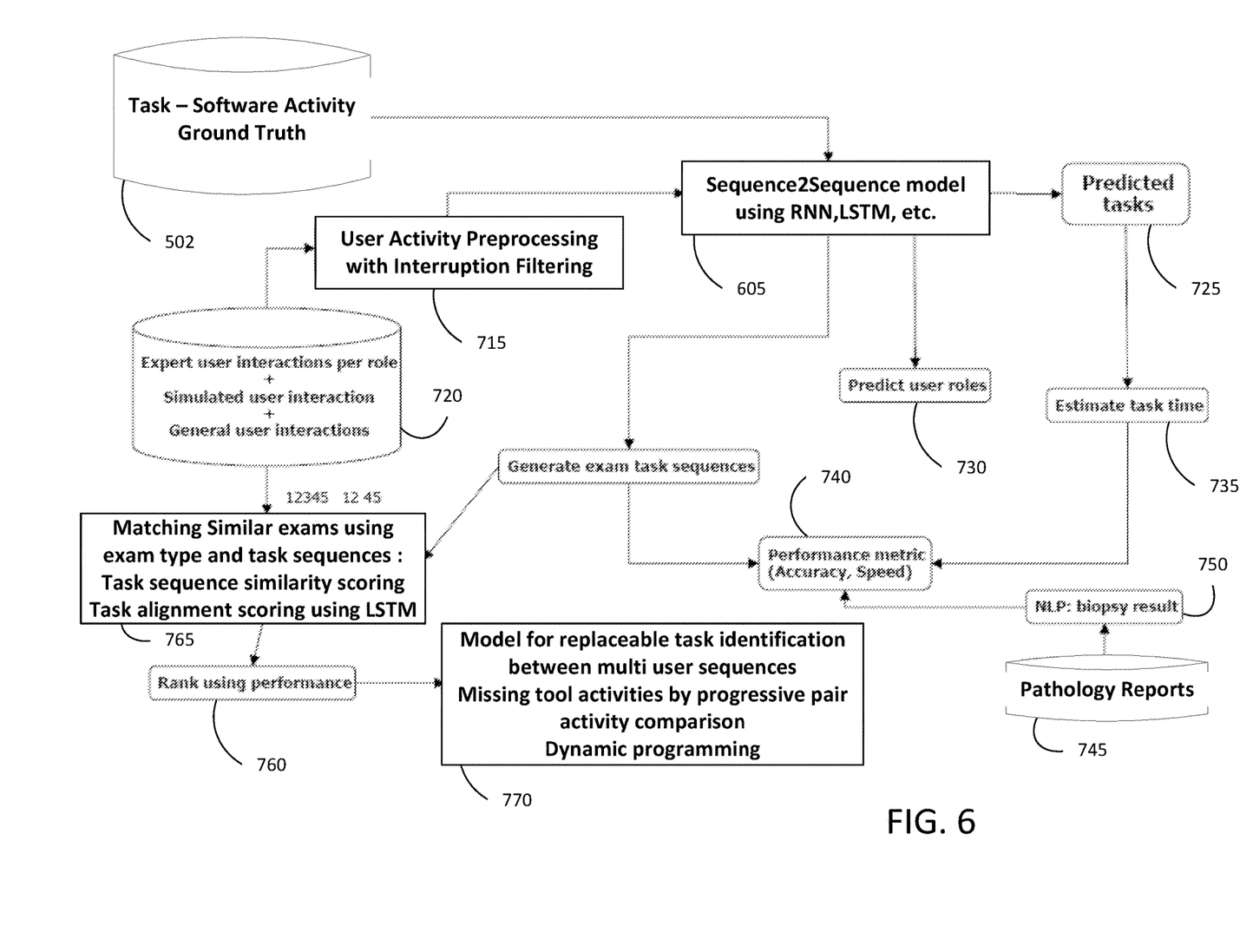
FIG. 6 illustrates a method of creating a time series model using the ground truth of FIG. 5 according to some embodiments.
Figure 7:
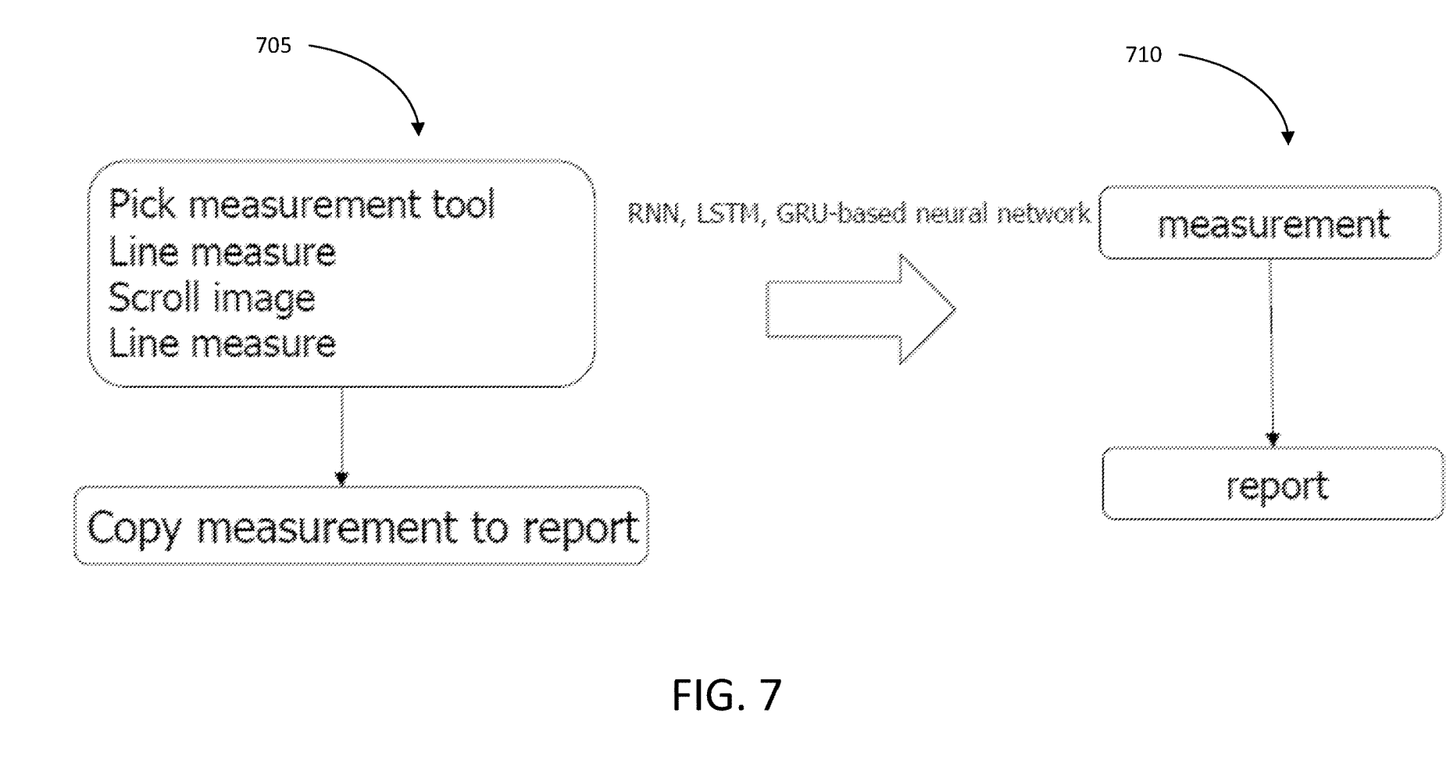
FIG. 7 illustrates an example mapping of user interactions to higher-level task(s) performed via the time series model of FIG. 6 according to some embodiments.

As illustrated in FIG. 6, the generated ground truth 502 may be used to create a time series model (represented in FIG. 6 by reference numeral 605) (sometimes referred to herein as a "Sequence2Sequence" model). The time series model 605 may be generated using one or more AI techniques, such as, for example, RNN, LSTM, TCN, or gated recurrent unit ("GRU"), or the like. After the time series model 605 is created, the time series model 605 may be used to predict task transition sequences of a user interacting with the software application based on, for example, observed interactions of the user. The task transition sequences may include higher-level tasks being performed by the user. For example, as illustrated in FIG. 7, the time series model 605 may be used to map a set of observed user interactions 705 to one or more higher-level task 710. In particular, using the example included in FIG. 4, observed user interactions 705 may include observing (or logging) the user selecting a measurement tool, making a line measurement, scrolling a displayed image, and making another line measurement before a measurement is copied to a report. As seen in FIG. 7, this sequence of user interactions (for example the user interactions 705) may be mapped via the time series model 605 to the higher-level task 710 of adding a measurement to a report.

Returning to FIG. 6, the time series model 605 receives (as input) user interactions (represented in FIG. 6 by reference numeral 715). The user interactions 715 may include, for example, interactions with the software application by a plurality of users, which may include expert users (for example, users with particular experience or skill levels), general users, simulated users (as part of verification test), or a combination thereof. In some embodiments, the user interactions 715 may represent multiple different user roles. In some embodiments, the user interactions 715 are captured in a system interaction log 720 that tracks and stores user actions. The user actions may include, for example, selections made by a user with the software application, data input by the user into the software application, and similar user actions, which may be associated with timestamps. Accordingly, as described in more detail below, the timestamps may be used to determine a sequence of user actions (i.e., a user interaction pattern or sequence). Returning to the example software application that includes a medical imaging application, the logged user interactions 715 may include actions taken by one or more radiologists while using the medical imaging application, such as, for example, accessing a worklist, viewing images, comparing images, viewing clinical information, performing a lesion measurement, creating a clinical report, interrupting workflow to view another exam in progress and consult with a technologist or referring doctor, completing peer review tasks, and the like.

As illustrated in FIG. 6, the user interactions 715 may undergo one or more preprocessing or filtering steps before being input to the time series model 605. In some embodiments, the processing includes identifying interruptions experienced by a particular user that may alter the user's interaction pattern or sequence. For example, when two sequential activities of a user are separated by a predetermined amount of time, this sequence may indicate that the user was interrupted (for example, by a co-worker, an urgent request received through another computing system, a need to consult with a technologist or a referring doctor, or the like) or otherwise had a period of inactivity and, thus, the entire sequence may be filtered from the user interactions 715 (as a way to avoid having such an interrupted workflow unduly impact optimization of the software application usage by the user using the systems and methods described herein). Similarly, in some embodiments, incomplete sequences where a user's log-in with the software application timed out or was manually terminated may be filtered as representing incomplete sequences. In addition, in some embodiments, observation sequences may be identified and filtered. For example, certain predetermined sequences of activities may be defined as representing mere observations (or at least as having a low probability of representing a task) and may be filtered from the user interactions 715.

After any such preprocessing or filtering, the user interactions 715 are input to the time series model 605. As described above, the times series model 605 may map an interaction pattern or sequence to a particular high-level task (as seen in FIG. 7). In other words, for a particular sequence of user interactions for a particular user, the time series model 605 may identify or "predict" the task being performed by the user (at 725 in FIG. 6). Similarly, as the ground truth 502 defined action sequences for tasks for particular user roles, the time series model 605 may also be trained to predict the user role for a particular user (at 730 of FIG. 6). For example, when a particular interaction sequence of a user is mapped (by the time series model 605) to a particular task (defined in the ground truth 502) for a particular user role, the role of the user may also be "predicted" (at 730 in FIG. 6).

As also illustrated in FIG. 6, after predicting a task being performed by a particular user with a particular user role (at 725 and 730), a time of the task may be estimated using the timestamps captured in the user interactions 715 (at 735). For example, when a sequence of user interactions X, Y, and Z are identified, via the time series model 605, as a user (of a particular user role) performing a particular task (for example, a generate report task), the timestamps associated with these user interactions (or at least the start and ending interaction) may be used to estimate the amount of time it took the user to perform the generate report task.

Similarly, one or more performance metrics may be generated for a particular task performed by a user (at 740). As one example, using the example above, when a user interaction associated with a particular user is identified, via the time series model 605, as being a generate report task, a diagnostic result may be accessed to determine an accuracy of the generated report. In some embodiments, pathology reports 745 may be accessed to obtain, for example, a biopsy result 750, which may be compared with a finding or diagnosis in the generated report to calculate an accuracy of the report (for example, represented as a binary value of accurate or not accurate or a percentage indicating amount of accuracy). Similarly, the time estimated for the task can be used to assign a speed metric to the task. As one example, different time ranges may be established that are used to determine whether an estimated time for a task is considered "fast," "normal," or "slow." Also, in some embodiments, a subset of the interactions may be used to generate a time-based performance metrics, such as a speed associated with taking a particular measurement. It should be understood that other ways to calculate or quantify performance metrics of a particular task may be used and, in some embodiments, different performance metrics may be used for different types of tasks, different user roles, different software applications, and the like.

With tasks, user roles, and performance metrics calculated based on the user interactions 715, activity sequences may be ranked based on one or more parameters (at 760), such as, for example, time required, diagnostic outcome, efficiency, accuracy, or the like. In some embodiments, the rankings may be performed for a particular type of exam. For example, performing the task of "generating a report" may involve different actions and sequences depending on the type of exam being studied and the associated type of report being generated. Accordingly, in some embodiments, an exam type may be determined for each user interaction 715 (i.e., identified task), such as based on the report generated as part of the test (at 745). The generated reports may be stored in one or more report repositories or may be inferred from the actions included within an identified task (for example, a certain action, set of actions, or sequence of actions may act as a signature for a task performed with respect to a particular exam type). It should be understood that other criteria for ranking tasks may be used, such as imaging modality used, body part being examined, patient demographics, user role, facility or network of related radiologists or imaging centers, or the like.

In some embodiments, to help ensure that similar tasks are being compared as part of the ranking, exam type and exam sequences may be used along with a similarity score or alignment score, which may be generated using a model, such as a LSTM trained to identify "similar" task sequences (for example, using training data with labeled sequences) (at 765).

The rankings resulting from this analysis may be output in various forms, mediums, and the like, including, for example, reports that may be displayed electronically within one or more user interfaces (for example, accessible by individual users, administrators, or both). The reports may be used to identify redundant or inefficient actions and may also optionally recommend alternative workflows for a particular user or group of users. For example, the state transitions for a particular user performing a task several times can be compared with observed sequences for other users, such as users identified as being experts or otherwise having predetermined performance metrics. This comparison may identify deficiencies of the user's typical activity sequence and, thus, may identify recommendations to make to the user for improving their interactions to improve efficiency, accuracy, or the like.

The analysis may also be used to perform continuous monitoring. As one example, the identified tasks, user roles, sequences, exam type, performance metrics, and the like, may be used as training information for a new model (an AI model), to train the model to identify "expert" user interactions as compared to "sub-optimal" user interactions and provide feedback to a user (for example, in real-time) to encourage a user to adapt and optimize their normal or standard behavior. In some embodiments, the model may be used to identify a replacement interaction sequence to recommend to user (after a task is performed or during performance of a task), identify missing actions by a user (for example, tools or software features not currently being used), or a combination thereof (at 770). Furthermore, as inference is performed on new cases, reports and test results may be collected to identify known patient outcomes (for example, biopsies). These known findings may be used to update performance feedback for users (for example, taking into account identified false negatives, false positives, particular detection rates, or the like). Similarly, when a predetermined number of new cases have been accumulated, a fine-tuning training epoch may be performed on the model to improve the rating system.

Alternatively or in addition, in some embodiments, the generated model may also be used to implement automatic actions. As one example, a determined expert sequence of interaction for a technique can be used to implement one or more automated quality measurements and/or summarizations (for example, to automate expert performance of a technician).

Furthermore, in addition to or as an alternative to behavior or interaction training or correction, embodiments described herein may be used to customize a user's interaction with the system, such as predicting next actions and providing a customized interface that allows the user to take the next action efficiently and accurately. Similarly, embodiments described herein may be used to track usage or effectiveness of new features, to detect obsolete features, or the like, which may be used to identify new features that may be needed, new trainings that could be useful, features that no longer need to be maintained (which reduces maintenance costs), or the like. For example, inefficiency may also arise from poor software design or a design that is not specific to the user's role. As one example, a radiologist may be shown an excessive amount of details about a patient and may always close some panels before starting work to avoid distractions.

Figure 8:
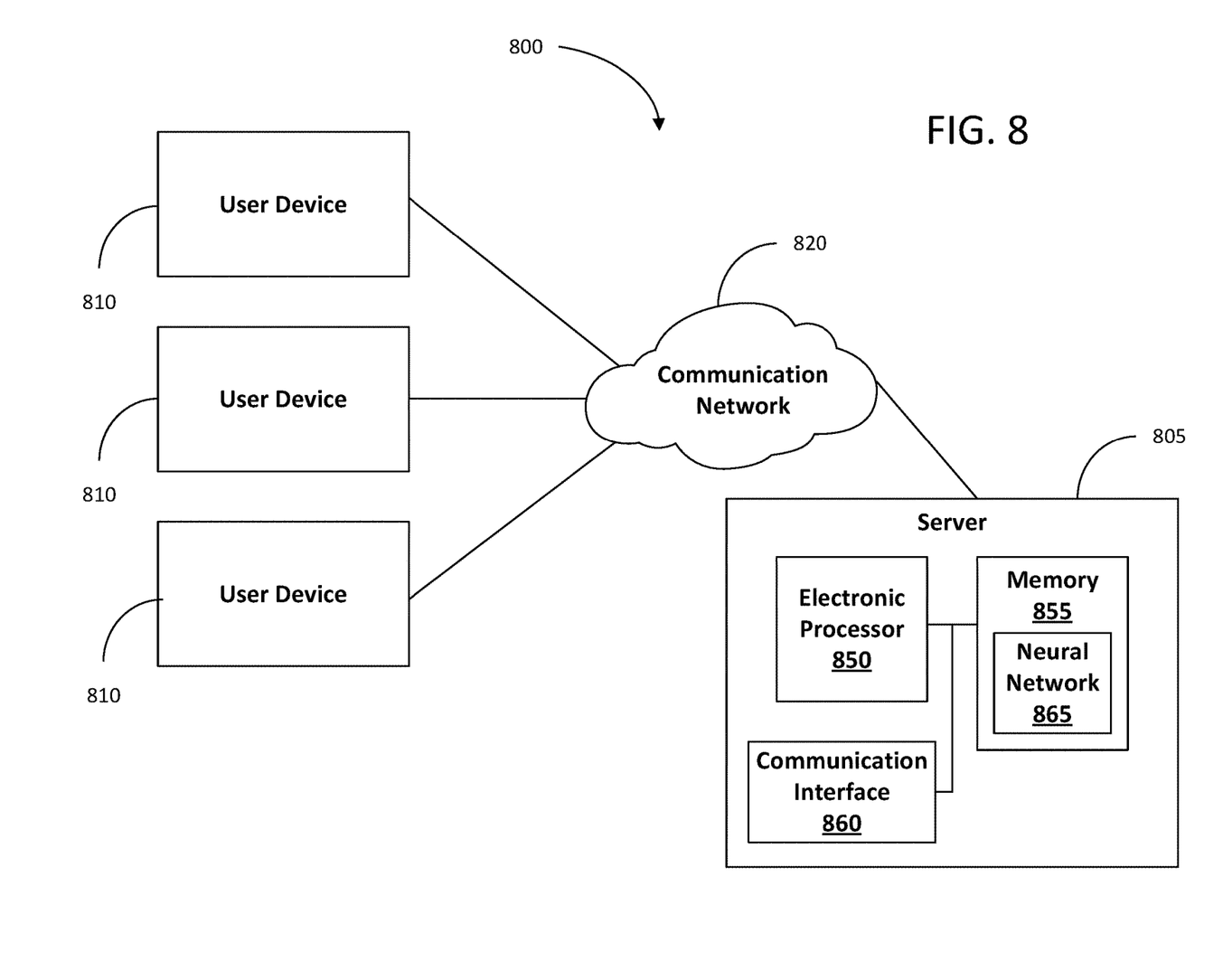
FIG. 8 illustrates an example system configuration for optimizing a user's interaction pattern with a software application using artificial intelligence according to some embodiments

As noted above, the functionality described above (for example, the methods of FIGS. 2-7 or a combination thereof) may be performed via one or more computing devices. FIG. 8 illustrates one example system 800 for optimizing user interactions with a software application according to some embodiments. As illustrated in FIG. 8, the system 800 includes a server 805 and one or more user devices 810. The server 805 and the user devices 810 communicate over one or more wired or wireless communication networks 820. Portions of the wireless communication networks 820 may be implemented using a wide area network, such as the Internet, a local area network, such as a Bluetooth™ network or Wi-Fi, and combinations or derivatives thereof. It should be understood that the system 800 may include more or fewer servers and the single server 805 illustrated in FIG. 8 is purely for illustrative purposes. For example, in some embodiments, the functionality described herein is performed via a plurality of servers in a distributed or cloud-computing environment. Similarly, it should be understood that the system 800 may include more or fewer servers and the three user devices 810 illustrated in FIG. 8 are purely for illustrative purposes. Furthermore, in some embodiments, the server 805, the user devices 810, or both may communicate with additional components within the system 800 (for example, over one or more wired or wireless connections). For example, in some embodiments, the server 810 may communicate with one or more external data repositories, such as one or more memory devices storing user activity logs, user software requirements, software verification tests, image studies, image study reports, pathology reports, user directories, or the like. In other embodiments, this data or portions thereof may be stored internal to the server 805.

It should also be understood that, in some embodiments, components included in the system 800 may communicate through one or more intermediary devices (not shown).

As illustrated in FIG. 8, the server 805 includes an electronic processor 850, a memory 855, and a communication interface 860. The electronic processor 850, the memory 855, and the communication interface 860 communicate wirelessly, over wired communication channels or buses, or a combination thereof. The server 805 may include additional components than those illustrated in FIG. 8 in various configurations. For example, in some embodiments, the server 805 includes multiple electronic processors, multiple memory modules, multiple communication interfaces, or a combination thereof. Also, it should be understood that the functionality described herein as being performed by the server 805 may be performed in a distributed nature by a plurality of computers located in various geographic locations. For example, the functionality described herein as being performed by the server 805 may be performed by a plurality of computers included in a cloud computing environment.

The electronic processor 850 may be, for example, a microprocessor, an application-specific integrated circuit ("ASIC"), and the like. The electronic processor 850 is generally configured to execute software instructions to perform a set of functions, including the functions described herein. The memory 855 includes a non-transitory computer-readable medium and stores data, including instructions executable by the electronic processor 850. The communication interface 860 may be, for example, a wired or wireless transceiver or port, for communicating over the communication network 820 and, optionally, one or more additional communication networks or connections.

Although not illustrated in FIG. 8, the user devices 810 may include similar components as the server 805. For example, like the server 805, each user device 810 may include one or more electronic processors, one or more memory modules, and one or more communication interfaces. In some embodiments, each user device 810 may include a desktop computer, a tablet computer, a smart phone, a smart watch or other wearable, a smart television, a smart whiteboard, or the like.

Returning to the server 805, in some embodiments, the electronic processor 850 executes an optimization application that performs the functionality described above. In some embodiments, the optimization application executes a collection of different models to perform the functionality described above, some of which may include deep learning models. For example, as illustrated in FIG. 8, the memory 855 of the server 805 stores one or more models, such as a neural network 865. The neural network 865 may be, for example, a two-dimensional ("2D") U-net architecture, a three-dimensional ("3D") convolutional neural network ("CNN"), a LSTM network, or the like.

Accordingly, some embodiments described herein provide a method for modeling expert software user interaction patterns using artificial intelligence. The method includes collecting a set of expert user software interaction time series data, classifying the data according to user roles and tasks being performed, and training an AI model to learn optimal sequences of interactions performed by users of each role for each task, the time required for each task, and the accuracy/outcome of the task. The method may also include optimizing the behavior of non-expert software users by receiving a set of non-expert user software interaction time series data for a current user and, using the AI model to classify the user's role and intended tasks for subsequences of the software interaction data, analyzing the differences between the current user's behavior and the learned behavior of experts with the same user role performing the same task, and generating a report describing the differences between the current user and expert users, and suggesting methods to optimize the user's behavior for time and accuracy.

Various features and advantages of the embodiments are set forth in the following claims.

What is claimed is:

1. A system for optimizing user interaction with a software application, the system comprising:
an electronic processor configured to:
  receive a collection of interaction data including a plurality of interaction sequences and data associated with each of the plurality of interaction sequences, wherein each of the interaction sequences relates to user interactions with a computer user interface when performing a task for a software function;
  determine, in a training operation of an artificial intelligence (AI) model, a user skill level performance metric representing the user's level of expertise for each of the plurality of interaction sequences according to an identified ground truth, wherein the performance metric is a value assigned to each of the plurality of interaction sequences representing a skill level of users performing each of the plurality of interaction sequences;
  train, with the collection of interaction data and the skill level performance metric determined for each of the plurality of interaction sequences as training data for performing supervised learning, the AI model to output a performance rating for a received interaction sequence, wherein the AI model is a time-series deep leaning model selected from the group consisting of a recurrent neural network model, a long short-term memory model, and a time-based convolution network model, and the training is provided to the time-series deep learning model, and wherein AI model is trained to learn an optimal sequence of interactions performed by an expert user by mapping each interaction sequence in the collection of interaction data to time and accuracy for each interaction sequence;
  receive a current interaction sequence of a user for the software application, apply the trained AI model to the current interaction pattern of the user to assign a performance rating to the current interaction sequence of the user based on comparing the current interaction sequences of the user to the optimal sequence of interactions learnt by the AI model during training;
  generate, via the AI model as applied to the current interaction pattern of the user, a recommendation for display within a user interface, for a modified user interaction pattern of the user for the software application based on the assigned performance rating;
  output feedback along with the recommendation to the use upon analyzing the current interaction sequence of the user;
  and retrain the AI model using the feedback.

2. The system of claim 1, wherein the performance rating includes at least one selected from a group consisting of a speed metric, an efficiency metric, and an accuracy metric.

3. The system of claim 1, wherein the electronic processor is configured to determine the performance metric by, for each interaction sequence included in the plurality of interaction sequences: predicting a user role for a user associated with the interaction sequence; predicting an intended task associated with the interaction sequence; and determining a time associated with performing the intended task.

4. The system of claim 3, wherein the electronic processor is configured to rank, for each user role and each intended task, each interaction sequence included in the plurality interaction sequences based on the performance metric.

5. The system of claim 4, wherein the electronic processor is configured to identify interaction sequences associated with an expert skill level based on the ranking of each interaction sequence.

6. The system of claim 5, wherein: the electronic processor is configured to generate the recommendation based on a comparison of the current interaction sequence to an interaction sequence included in the collection of interaction data; and the interaction sequence is associated with the same task and user role associated with the current interaction sequence.

7. The system of claim 1, wherein the electronic processor is configured to: predict a user role for the user associated with the current interaction sequence; predict an intended task associated with the current interaction sequence; and determine a performance metric associated with the current interaction sequence.

8. A method for optimizing user interaction with a software application, the method comprising:
   receiving, with an electronic processor, a collection of interaction data including a plurality of interaction sequences and data associated with each of the plurality of interaction sequences, wherein each of the interaction sequences relates to user interactions with a computer user interface when performing a task for a software function;
   determining, in a training operation of an artificial intelligence (AI) model with the electronic processor, a user skill level performance metric representing the user's level of expertise for each of the plurality of interaction sequences according to an identified ground truth, wherein the performance metric is a value assigned to each of the plurality of interaction sequences representing a skill level of users performing each of the plurality of interaction sequences;
   training, with the electronic processor, with the collection of interaction data and the skill level performance metric determined for each of the plurality of interaction sequences, as training data for performing supervised learning, the AI model to output a performance rating for a received interaction sequence, wherein the AI model is a time-series deep leaning model selected from the group consisting of a recurrent neural network model, a long short-term memory model, and a time-based convolution network model, and the training is provided to the time-series deep learning model, and wherein AI model is trained to learn an optimal sequence of interactions performed by an expert user by mapping each interaction sequence in the collection of interaction data to time and accuracy for each interaction sequence;
   receiving, with the electronic processor, a current interaction sequence of a user for the software application;
   applying the trained AI model with the electronic processor, to the current interaction pattern of the user to assign a performance rating to the current interaction sequence of the user based on comparing the current interaction sequences of the user to the optimal sequence of interactions learnt by the AI model during training;
   generating, with the electronic processor, via the AI model as applied to the current interaction pattern of the user, a recommendation for display within a user interface, for a modified user interaction pattern of the user for the software application based on the assigned performance rating;
   outputting, with the electronic processor, feedback along with the recommendation to the use upon analyzing the current interaction sequence of the user;
   and retraining, with the electronic processor, the AI model using the feedback.

9. The system of claim 8, wherein the determining of the performance metric comprises: for each interaction sequence included in the plurality of interaction sequences: predicting a user role for a user associated with the interaction sequence; predicting an intended task associated with the interaction sequence; and determining a time associated with performing the intended task.

10. The system of claim 9, further comprising: ranking, for each user role and each intended task, each interaction sequence included in the plurality interaction sequences based on the performance metric.

11. The system of claim 8, further comprising: predicting a user role for the user associated with the current interaction sequence; predicting an intended task associated with the current interaction sequence; and determining a performance metric associated with the current interaction sequence; wherein the recommendation is based on the performance metric associated with the current interaction sequence.

12. A non-transitory, computer-readable medium storing instructions that, when executed by an electronic processor, perform a set of functions, the set of functions comprising:
   receiving a collection of interaction data including a plurality of interaction sequences and data associated with each of the plurality of interaction sequences, wherein each of the interaction sequences relates to user interactions with a computer user interface when performing a task for a software function;
   determining, in a training operation of an artificial intelligence (AI) model, a user skill level performance metric representing the user's level of expertise for each of the plurality of interaction sequences according to an identified ground truth, wherein the performance metric is a value assigned to each of the plurality of interaction sequences representing a skill level of users performing each of the plurality of interaction sequences;
   training with the collection of interaction data and the skill level performance metric determined for each of the plurality of interaction sequences as training data for performing supervised learning, the AI model to output a performance rating for a received interaction sequence, wherein the AI model is a time-series deep leaning model selected from the group consisting of a recurrent neural network model, a long short-term memory model, and a time-based convolution network model, and the training is provided to the time-series deep learning model, and wherein AI model is trained to learn an optimal sequence of interactions performed by an expert user by mapping each interaction sequence in the collection of interaction data to time and accuracy for each interaction sequence;
   receiving a current interaction sequence of a user for the software application;
   applying the trained AI model to the current interaction pattern of the user to assign a performance rating to the current interaction sequence of the user based on comparing the current interaction sequences of the user to the optimal sequence of interactions learnt by the AI model during training;
   generating via the AI model as applied to the current interaction pattern of the user, a recommendation, for display within a user interface, for a modified user interaction pattern of the user for the software application based on the assigned performance rating;
   outputting feedback along with the recommendation to the use upon analyzing the current interaction sequence of the user;
   and retraining the AI model using the feedback.

13. The computer-readable medium of claim 12, wherein the determining of the performance metric comprises: for each interaction sequence included in the plurality of interaction sequences: predicting a user role for a user associated with the interaction sequence; predicting an intended task associated with the interaction sequence; and determining a time associated with performing the intended task.

14. The computer-readable medium of claim 13, the set of functions further comprising: ranking, for each user role and each intended task, each interaction sequence included in the plurality interaction sequences based on the performance metric.

15. The computer-readable medium of claim 14, the set of functions further comprising: identifying interaction sequences associated with an expert skill level based on the ranking of each interaction sequence.

16. The computer-readable medium of claim 15, wherein: the generating of the recommendation includes generating the recommendation based on a comparison of the current interaction sequence to an interaction sequence included in the collection of interaction data; the interaction sequence is associated with the same task and user role associated with the current interaction sequence; and the AI model is a time-series deep learning model.

17. The system of claim 1, wherein the time-series deep learning model is the recurrent neural network model, and the training is provided to the recurrent neural network model.

18. The system of claim 1, wherein the time-series deep learning model is the long short-term memory model, and the training is provided to the long short-term memory model.

19. The system of claim 1, wherein the time-series deep learning model is the time-based convolution network model, and the training is provided to the time-based convolution network model.

* * * * *